United States Patent
Harichian

(10) Patent No.: US 8,648,025 B2
(45) Date of Patent: *Feb. 11, 2014

(54) PERSONAL CARE COMPOSITIONS WITH SILICONES AND POLYHYDROXY QUATERNARY AMMONIUM SALTS

(71) Applicant: Conopco, Inc., Englewood Cliffs, NJ (US)

(72) Inventor: Bijan Harichian, Brookfield, CT (US)

(73) Assignee: Conopco, Inc., Englewood Cliffs, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/679,233

(22) Filed: Nov. 16, 2012

(65) Prior Publication Data

US 2013/0129645 A1 May 23, 2013

Related U.S. Application Data

(60) Provisional application No. 61/562,482, filed on Nov. 22, 2011.

(51) Int. Cl.
| | | |
|---|---|---|
| A61Q 19/10 | (2006.01) | |
| A61Q 17/04 | (2006.01) | |
| A61Q 1/10 | (2006.01) | |
| A61Q 5/12 | (2006.01) | |
| A61Q 5/02 | (2006.01) | |
| C11D 1/62 | (2006.01) | |

(52) U.S. Cl.
USPC ......... 510/130; 424/59; 424/70.7; 424/70.12; 424/70.28; 510/119; 510/123; 510/504

(58) Field of Classification Search
USPC ............. 424/59, 70.7, 70.12, 70.28; 510/119, 510/130, 123, 504
See application file for complete search history.

(56) References Cited

U.S. PATENT DOCUMENTS

| | | |
|---|---|---|
| 5,089,578 A | 2/1992 | Valint et al. |
| 5,135,747 A | 8/1992 | Faryniarz |
| 5,686,082 A | 11/1997 | N'Guyen |
| 5,833,999 A | 11/1998 | Trinh |
| 5,849,310 A | 12/1998 | Trinh et al. |
| 5,891,452 A | 4/1999 | Sebillote-Arnaud et al. |
| 5,952,395 A | 9/1999 | Lorant |
| 5,961,961 A | 10/1999 | Dobkowski et al. |
| 6,086,903 A | 7/2000 | Trinh et al. |
| 6,100,233 A | 8/2000 | Sivik |
| 6,869,977 B1 | 3/2005 | O'Lenick, Jr. et al. |
| 7,175,834 B2 | 2/2007 | Aust et al. |
| 7,659,233 B2 * | 2/2010 | Hurley et al. ................. 510/130 |
| 8,124,063 B2 | 2/2012 | Harichian et al. |
| 8,173,108 B2 | 5/2012 | Misso et al. |
| 8,206,691 B2 | 6/2012 | Polonka et al. |
| 2007/0053853 A1 * | 3/2007 | Hurley et al. ................. 424/59 |
| 2012/0259011 A1 | 10/2012 | Misso |

FOREIGN PATENT DOCUMENTS

| | | |
|---|---|---|
| EP | 750899 A2 | 1/1997 |
| WO | WO0031154 | 6/2000 |
| WO | WO0243689 A2 | 6/2002 |
| WO | WO2012050769 A1 | 4/2012 |

OTHER PUBLICATIONS

Co-Pending U.S. Appl. No. 61/562,455, filed Nov. 22, 2011; titled "Thickened Cosmetic Compositions".
Co-Pending U.S. Appl. No. 61/562,470, filed Nov. 22, 2011; titled "Glow and Sunless Tanning Color Enhancement by Polyhydroxy Quaternary Ammonium Salts".
Co-Pending U.S. Appl. No. 61/562,473, filed Nov. 22, 2011; titled "Sunscreen Composition With Polyhydroxy Quaternary Ammonium Salts".
Co-Pending U.S. Appl. No. 61/562,475, filed Nov. 22, 2011; titled "Foam Enhancement of Mild Surfactants with Polyhydroxy Quaternary Ammonium Salts".
Co-Pending U.S. Appl. No. 61/562,479, filed Nov. 22, 2011; titled "Preservative System Enhanced With Polyhydroxy Quaternary Ammonium Salts".
Co-Pending U.S. Appl. No. 61/562,481, filed Nov. 22, 2011; titlted "Personal Care Compositions With Enhanced Fragrance Delivery Via Polyhydroxy Quaternary Ammonium Salts".

* cited by examiner

*Primary Examiner* — Ernst Arnold
*Assistant Examiner* — Kyung Sook Chang
(74) *Attorney, Agent, or Firm* — Edward A. Squillante, Jr.

(57) ABSTRACT

A personal care composition is provided with a silicone compound and being aesthetically modified for improved skinfeel with a polyhydroxy quaternary ammonium salt of structure (I):

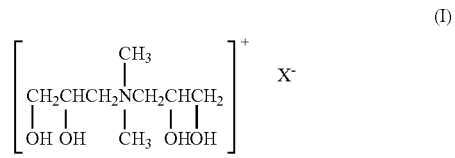

wherein $X^-$ is selected from the group consisting of chloride, bromide, hydroxyl, sulphate, phosphate, methosulphate, carboxyl, citrate and tartrate; and
(ii) from about 0.05 to about 50% of silicone by weight of the composition.

7 Claims, No Drawings

PERSONAL CARE COMPOSITIONS WITH SILICONES AND POLYHYDROXY QUATERNARY AMMONIUM SALTS

BACKGROUND OF THE INVENTION

1. Field of the Invention

The invention concerns personal care compositions formulated to impart moisturization and having excellent skinfeel properties.

2. The Related Art

Dry skin is a problem in varying degree to most humans. This condition is particularly evident in winter. Personal care products such as skin creams/lotions, shampoos/conditioners, toilet bars/shower gels and antiperspirants/deodorants are normally formulated with at least one material to address dry skin. Symptoms such as itching, flaking and a visually displeasing dermal appearance can all to some extent be modulated.

There are three traditional classes of materials employed against the problem. Occlusives such as petrolatum or silicone oils serve to inhibit loss of natural moisture. They form a barrier between the epidermis and the environment. Another approach is the use of keratolytic agents to enhance rate of dermal exfoliation. Alpha-hydroxy acids are the most common agents for achieving exfoliation.

A third approach to dry skin is topical application of humectants. Hydroxylated monomeric and polymeric organic substances are generally used for this purpose. Glycerin known also as glycerol is one of the most effective humectants.

Quaternary ammonium compounds have recently been commercialized as moisturizers. One of these known under the trademark Honeyquat 50 with INCI name of Hydroxypropyltrimonium Honey has been reported to be a better humectant than glycerin at levels of 2%. See the Arch/Brooks brochure titled "Cosmetic Ingredients & Ideas®", Issue No. 2, August 2001. Honeyquat 50 is described as being derived from the reaction of pendent hydroxyl groups (on the disaccharide) of a "light" deodorized grade of honey with a chlorohydroxytrimethylammonium derivative. Another commercial quaternary ammonium moisturizer is Cola™ Moist 200 with INCI name of Hydroxypropyl Bis-Hydroxyethyldimonium Chloride. See the Colonial Chemical Inc. brochure titled "Cola™ Moist 200", copyright 2004. U.S. Pat. No. 6,869,977 B1 (O'Lenick, Jr. et al.) to Colonial Chemical Inc. discloses a related monocationic material described as a moisturizing agent.

In there, the U.S. Pat. No. 7,659,233 B2 (Hurley et al.) discloses a composition that combines silicones with dihydroxypropyl trialkyl ammonium salts to deliver improved skinfeel properties. Although a significant advance, there is room for an improvement over this technology.

Many moisturizing actives impart to their formulas an aesthetically displeasing tack and/or sticky skinfeel. The present invention sought to provide a silicone containing moisturizing personal care composition having consumer pleasing skinfeel properties.

SUMMARY OF THE INVENTION

A personal care composition is provided which includes:
(i) from about 0.05% to about 30% by weight of a polyhydroxy quaternary ammonium salt of structure (I):

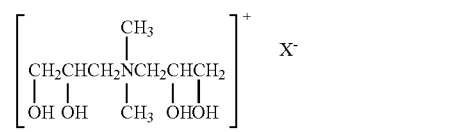

wherein X⁻ is selected from the group consisting of chloride, bromide, hydroxyl, sulphate, phosphate, methosulphate, carboxyl, citrate and tartrate; and
(ii) from about 0.05 to about 50% by weight of a silicone.

DETAILED DESCRIPTION OF THE INVENTION

Now it has been found that combinations of silicones with polyhydroxy quaternary ammonium salts of structure (I) can significantly improve skinfeel properties of personal care compositions.

Accordingly, a first essential element of the present invention is that of a polyhydroxy quaternary ammonium salt of structure (I) as follows:

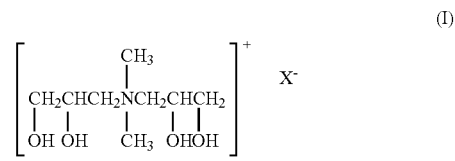

wherein X⁻ is selected from the group consisting of chloride, bromide, hydroxyl, sulphate, phosphate, methosulphate, carboxyl, citrate and tartrate. Most preferred is bis(dihydroxypropyl)dimethylammonium chloride.

Amounts of the polyhydroxy quaternary ammonium salts may range from about 0.05 to about 30%, preferably from about 0.1 to about 25%, more preferably from about 5 to about 20%, optimally from about 10 to about 15% by weight of the composition.

The moisturizing compositions of this invention will include a silicone. A wide variety of silicones including materials of liquid, solid or semi-solid consistency at room temperature can be useful for this invention. Liquid silicones include silicone oils which may be divided into the volatile and nonvolatile variety. The term "volatile" as used herein refers to those materials which have a measurable vapor pressure at ambient temperature. Volatile silicone oils are preferably chosen from cyclic (cyclomethicone) or linear polydimethylsiloxanes containing from 3 to 9, preferably from 4 to 5, silicon atoms. Commercially available volatile silicone oils include DC 200, DC 244, DC 245, DC 344 and DC 345, all supplied by the Dow Corning Corporation; SF-1204, SF-1202 Silicone Fluids, GE 7207 and GE 7158 sourced from GE Silicones; and SWS-03314 sourced from SWS Silicones Corporation.

Useful nonvolatile silicone oils include polyalkyl siloxanes, polyalkylaryl siloxanes and polyether siloxane copolymers. The essentially nonvolatile polyalkyl siloxanes useful herein include, for example, polydimethyl siloxanes with viscosities of from about $5\times10^{-6}$ to $0.1$ m$^2$/s at 25° C. Among the preferred nonvolatile emollients useful in the present compositions are the polydimethyl siloxanes having viscosities from about $1\times10^{-5}$ to about $4\times10^{-4}$ m$^2$/s at 25° C. Representative commercial materials include polyalkyl siloxanes sold under the Viscasil Series from G.E. Silicones, and the DC 200 series sold by the Dow Corning Corporation. Polyalkylaryl siloxanes including polymethylphenyl siloxanes such as SF 1075 methyl-phenyl fluid and 556 Cosmetic Grade Fluid (sold by Dow Corning Corporation) may also be useful. Illustrative polyoxyalkylene ether copolymers are commercially available as SF 1066 from G.E. Silicones, and PEG-10 Dimethicone available from Shin-Etsu.

Another class of nonvolatile silicones are emulsifying and non-emulsifying silicone elastomers. Representative of this category is Dimethicone/Vinyl Dimethicone Crosspolymer available as Dow Corning 9040, General Electric SFE 839, and Shin-Etsu KSG-18. Silicone waxes such as Silwax WS-L (Dimethicone Copolyol Laurate) may also be useful.

Amounts of the silicone may range from about 0.05 to about 50%, preferably from about 0.5 to about 40%, more preferably from about 2 to about 20%, optimally from about 5 to about 12% by weight of the composition.

Emollient materials may serve as cosmetically acceptable carriers. These may be in the form of natural or synthetic esters and hydrocarbons. Amounts of the emollients may range anywhere from about 0.1 to about 60%, preferably between about 1 and about 30% by weight of the composition.

Among the ester emollients are:

(a) Alkyl esters of saturated fatty acids having 10 to 24 carbon atoms. Examples thereof include behenyl neopentanoate, isononyl isonanonoate, isopropyl myristate and octyl stearate.

(b) Ether-esters such as fatty acid esters of ethoxylated saturated fatty alcohols.

(c) Polyhydric alcohol esters. Ethylene glycol mono and di-fatty acid esters, diethylene glycol mono- and di-fatty acid esters, polyethylene glycol (200-6000) mono- and di-fatty acid esters, propylene glycol mono- and di-fatty acid esters, polypropylene glycol 2000 monostearate, ethoxylated propylene glycol monostearate, glyceryl mono- and di-fatty acid esters, polyglycerol poly-fatty esters, ethoxylated glyceryl mono-stearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters. Particularly useful are pentaerythritol, trimethylolpropane and neopentyl glycol esters of $C_1$-$C_{30}$ alcohols.

(d) Wax esters such as beeswax, spermaceti wax and tribehenin wax.

(e) Sugar ester of fatty acids such as sucrose polybehenate and sucrose polycottonseedate.

Natural ester emollients principally are based upon mono-, di- and tri-glycerides. Representative glycerides include sunflower seed oil, cottonseed oil, borage oil, borage seed oil, primrose oil, castor and hydrogenated castor oils, rice bran oil, soybean oil, olive oil, safflower oil, shea butter, jojoba oil and combinations thereof. Animal derived emollients are represented by lanolin oil and lanolin derivatives. Amounts of the natural esters may range from about 0.1 to about 20% by weight of the compositions.

Hydrocarbons which are suitable cosmetically acceptable carriers include petrolatum, mineral oil, $C_{11}$-$C_{13}$ isoparaffins, polybutenes, and especially isohexadecane, available commercially as Permethyl 101A from Presperse Inc.

Fatty acids having from 10 to 30 carbon atoms may also be suitable as cosmetically acceptable carriers. Illustrative of this category are pelargonic, lauric, myristic, palmitic, stearic, isostearic, oleic, linoleic, linolenic, hydroxystearic and behenic acids.

Surfactants may also be present in compositions of the present invention. Total concentration of the surfactant when present may range from about 0.1 to about 50%, preferably from about 1 to about 25%, optimally from about 1 to about 10% by weight of the composition, and being highly dependent upon the type of personal care product. The surfactant may be selected from the group consisting of anionic, nonionic, cationic and amphoteric actives. Particularly preferred nonionic surfactants are those with a $C_{10}$-$C_{20}$ fatty alcohol or acid hydrophobe condensed with from 2 to 100 moles of ethylene oxide or propylene oxide per mole of hydrophobe; $C_2$-$C_{10}$ alkyl phenols condensed with from 2 to 20 moles of alkylene oxide; mono- and di-fatty acid esters of ethylene glycol; fatty acid monoglyceride; sorbitan, mono- and di-$C_8$-$C_{20}$ fatty acids; and polyoxyethylene sorbitan as well as combinations thereof. Alkyl polyglycosides and saccharide fatty amides (e.g. methyl gluconamides) and trialkylamine oxides are also suitable nonionic surfactants.

Preferred anionic surfactants include soap, alkyl ether sulfates and sulfonates, alkyl sulfates and sulfonates, alkylbenzene sulfonates, alkyl and dialkyl sulfosuccinates, $C_8$-$C_{20}$ acyl isethionates, $C_8$-$C_{20}$ alkyl ether phosphates, $C_8$-$C_{20}$ sarcosinates, $C_8$-$C_{20}$ acyl lactylates, sulfoacetates and combinations thereof.

Useful amphoteric surfactants include cocoamidopropyl betaine, $C_{12}$-$C_{20}$ trialkyl betaines, sodium lauroamphoacetate, and sodium laurodiamphoacetate.

Adjunct humectants may be employed in the present invention. These are generally polyhydric alcohol-type materials. Typical polyhydric alcohols include glycerin, propylene glycol, dipropylene glycol, polypropylene glycol, polyethylene glycol, sorbitol, hydroxypropyl sorbitol, hexylene glycol, 1,3-butylene glycol, isoprene glycol, 1,2,6-hexanetriol, ethoxylated glycerol, propoxylated glycerol and mixtures thereof. The amount of adjunct humectant may range anywhere from about 0.2 to about 40%, preferably between 1 and 25%, most preferably between 2 and 15% by weight of the composition. Most preferred is glycerin as an adjunct humectant or moisturizer.

Sunscreen agents may also be included in compositions of the present invention. Particularly preferred are such materials as ethylhexyl p-methoxycinnamate, available as Parsol MCX®, Avobenzene available as Parsol 1789®, and benzophenone-3 also known as Oxybenzone. Inorganic sunscreen actives may be employed such as microfine (1 to 100 nm) titanium dioxide and zinc oxide. Amounts of the sunscreen agents when present may generally range from 0.1 to 30%, preferably from 2 to 20%, optimally from 4 to 10% by weight of the composition.

Antiperspirants and deodorant compositions of the present invention ordinarily will contain astringent actives. Examples include aluminum chloride, aluminum chlorhydrex, aluminum-zirconium chlorhydrex glycine, aluminum sulfate, zinc sulfate, zirconium and aluminum chlorohydroglycinate, zirconium hydroxychloride, zirconium and aluminum lactate, zinc phenolsulfonate and combinations thereof. Amounts of the astringents may range anywhere from about 0.5 to about 50% by weight of the composition.

Dental products formulated according to the present invention will generally contain a fluoride source to prevent dental caries. Typical anti-caries actives include sodium fluoride, stannous fluoride and sodium monofluoro phosphate.

Amounts of these materials will be determined by the amount of fluoride releasable which should range between about 500 to about 8800 ppm of the composition. Other components of dentifrices can include desensitizing agents such as potassium nitrate and strontium nitrate, sweeteners such as sodium saccharine, aspartame, sucralose, and potassium acesulfam. Thickeners, opacifying agents, abrasives and colorants will normally also be present.

Preservatives can desirably be incorporated into the personal care compositions of this invention to protect against the growth of potentially harmful microorganisms. Particularly preferred preservatives are phenoxyethanol, methyl paraben, propyl paraben, imidazolidinyl urea, dimethyloldimethylhydantoin, ethylenediaminetetraacetic acid salts (EDTA), sodium dehydroacetate, methylchloroisothiazolinone, methylisothiazolinone, iodopropynbutylcarbamate and benzyl alcohol. The preservatives should be selected having regard for the use of the composition and possible incompatibilities between the preservatives and other ingredients. Preservatives are preferably employed in amounts ranging from 0.0001% to 2% by weight of the composition.

Compositions of the present invention may include vitamins. Illustrative vitamins are Vitamin A (retinol), Vitamin $B_2$, Vitamin $B_3$ (niacinamide), Vitamin $B_6$, Vitamin C, Vitamin E, Folic Acid and Biotin. Derivatives of the vitamins may also be employed. For instance, Vitamin C derivatives include ascorbyl tetraisopalmitate, magnesium ascorbyl phosphate and ascorbyl glycoside. Derivatives of Vitamin E include tocopheryl acetate, tocopheryl palmitate and tocopheryl linoleate. DL-panthenol and derivatives may also be employed. Total amount of vitamins when present in compositions according to the present invention may range from 0.001 to 10%, preferably from 0.01% to 1%, optimally from 0.1 to 0.5% by weight of the composition.

Another type of useful substance can be that of an enzyme such as amylases, oxidases, proteases, lipases, cellulases, elastases and combinations.

Skin lightening compounds may be included in the compositions of the invention. Illustrative substances are placental extract, lactic acid, niacinamide, arbutin, kojic acid, ferulic acid, resorcinol and derivatives including 4-substituted resorcinols and combinations thereof. Amounts of these agents may range from about 0.1 to about 10%, preferably from about 0.5 to about 2% by weight of the composition.

Desquamation promoters may be present. Illustrative are the alpha-hydroxycarboxylic acids and beta-hydroxycarboxylic acids. The term "acid" is meant to include not only the free acid but also salts and $C_1$-$C_{30}$ alkyl or aryl esters thereof and lactones generated from removal of water to form cyclic or linear lactone structures. Representative acids are glycolic, lactic and malic acids. Salicylic acid is representative of the beta-hydroxycarboxylic acids. Amounts of these materials when present may range from about 0.01 to about 15% by weight of the composition.

A variety of herbal extracts may optionally be included in compositions of this invention. The extracts may either be water soluble or water-insoluble carried in a solvent which respectively is hydrophilic or hydrophobic. Water and ethanol are the preferred extract solvents. Illustrative extracts include those from green tea, chamomile, licorice, aloe vera, grape seed, citrus unshui, willow bark, sage, thyme and rosemary.

Also included may be such materials as lipoic acid, retinoxytrimethylsilane (available from Clariant Corp. under the Silcare 1M-75 trademark), dehydroepiandrosterone (DHEA) and combinations thereof. Ceramides (including Ceramide 1, Ceramide 3, Ceramide 3B and Ceramide 6) as well as pseudoceramides may also be useful. Amounts of these materials may range from about 0.000001 to about 10%, preferably from about 0.0001 to about 1% by weight of the composition.

Colorants, opacifiers and abrasives may also be included in compositions of the present invention. Each of these substances may range from about 0.05 to about 5%, preferably between 0.1 and 3% by weight of the composition.

Personal care compositions of the present invention may be in any form. These forms may include lotions, creams, roll-on formulations, sticks, mousses, aerosol and non-aerosol sprays and fabric (e.g. nonwoven textile)-applied formulations.

A wide variety of packaging can be employed to store and deliver the personal care compositions. Packaging is often dependent upon the type of personal care end-use. For instance, leave-on skin lotions and creams, shampoos, hair conditioners and shower gels generally employ plastic containers with an opening at a dispensing end covered by a closure. Typical closures are screw-caps, non-aerosol pumps and flip-top hinged lids. Packaging for antiperspirants, deodorants and depilatories may involve a container with a roll-on ball on a dispensing end. Alternatively these types of personal care products may be delivered as a stick composition formulation in a container with propel-repel mechanism where the stick moves on a platform towards a dispensing orifice. Metallic cans pressurized by a propellant and having a spray nozzle serve as packaging for antiperspirants, shave creams and other sprayable personal care products. Toilet bars may have packaging constituted by a cellulosic or plastic wrapper or within a cardboard box or even encompassed by a shrink wrap plastic film.

Another aspect of compositions of this invention may be the inclusion of instructions attached to or otherwise associated with the packaging. The instructions indicate to a consumer topical use of the composition on skin, hair or oral mucosae. Packaging itself will usually be printed with the instructions but sometimes a separate written insert within the package may serve to provide the instructions. Typical language includes phrases such as "apply a thin layer to the underarm", "apply regularly to hands", "apply to wet hair, lather and rinse", "cleanse skin" and "pump a small amount onto the palm of your hand".

The term "comprising" is meant not to be limiting to any subsequently stated elements but rather to encompass non-specified elements of major or minor functional importance. In other words the listed steps, elements or options need not be exhaustive. Whenever the words "including" or "having" are used, these terms are meant to be equivalent to "comprising" as defined above.

Except in the operating and comparative examples, or where otherwise explicitly indicated, all numbers in this description indicating amounts of material ought to be understood as modified by the word "about".

All documents referred to herein, including all patents, patent applications, and printed publications, are hereby incorporated by reference in their entirety in this disclosure.

The following examples will more fully illustrate the embodiments of this invention. All parts, percentages and proportions referred to herein and in the appended claims are by weight unless otherwise illustrated.

EXAMPLE 1

Synthesis of Bis-(2,3-dihydroxypropyl)dimethylammonium Chloride

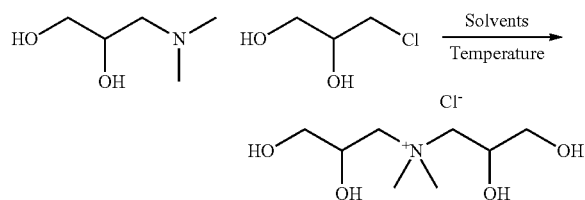

General Procedure:

Dimethylaminopropanediol (20 g, 0.168 moles) and 3-Chloropropane-1,2-diol (18.5 g, 0.168 moles) were stirred in ethanol (40 mL) at 70° C. until the reaction is complete. The reaction was monitored by LCMS. Upon completion, the reaction was allowed to cool and the solution was poured to a mixture of acetone:methyl-tert-butyl ether (2:1, 300 mL) to oil out the product. The Supernatant was decanted and product was washed with a mixture of acetone/methyl-tert-butyl ether (2×300 mL). The oil obtained was dried over high vacuum followed by freeze drying to obtain colorless oil/semisolid (>90% yield). The pure product was characterized using $^1$H NMR, $^{13}$C NMR, and MS. Details on characterization as follows.

Analytical Instrumentation Used:

LC MS: The MS of the compound was recorded using a Micromass Quattro Ultima LCMS system with Mass Lynx 4.1 software equipped with Agilent 1100 LC system. A solution of 50 ppm was infused in the LCMS system using 50:50 Methanol: 5 mM HCOOH as the mobile phase and ESI positive source.

NMR: A sample (144 mg) was dissolved in $D_2O$ (650 mL) and analyzed by $^1$H and $^{13}$C NMR using a Varian Eft-60 NMR Spectrometer (60 MHz) and the data processed using Nuts Pro (2D Professional version, Acorn NMR).

Characterization of Bis-(2.3-dihydroxypropyl)dimethylammonium Chloride $^1$H NMR ($D_2O$, 60 MHz) □ 3.22 (s, 6H, $CH_3$), 3.48 (s, 4H, $CH_2$), 3.57 (s, 4H, $CH_2$), 4.2 (bm, 2H, —CH), $^{13}$C NMR ($D_2O$) □ 52.72 ($CH_{3',s}$), 63.55 (-$CH_2$), 65.97 (—CH), 67.24 (—$CH_{2',s}$)

LCMS (M-Cl) 194.25 (calcd), 194.22 (observed).

EXAMPLE 2

Illustrated herein is a skin cream incorporating a quat salt and silicone of the present invention.

TABLE I

| INGREDIENT | WEIGHT % |
| --- | --- |
| Glycerin | 15.00 |
| Niacinamide | 5.00 |
| Bis(dihydroxypropyl)dimethylammonium chloride | 5.00 |
| Permethyl 101A[1] | 3.00 |
| Sepigel 305[2] | 2.50 |
| Q2-1403[3] | 2.00 |
| Linseed Oil | 1.33 |
| Arlatone 2121[4] | 1.00 |
| Cetyl Alcohol CO-1695 | 0.72 |
| SEFA Cottonate[5] | 0.67 |
| Tocopherol Acetate | 0.50 |
| Panthenol | 0.50 |
| Stearyl Alcohol | 0.48 |
| Titanium Dioxide | 0.40 |
| Disodium EDTA | 0.10 |
| Glydant Plus[6] | 0.10 |
| PEG-100 Stearate | 0.10 |
| Stearic Acid | 0.10 |
| Purified Water | Balance |

[1]Isohexadecane, Presperse Inc., South Plainfield, NJ
[2]Polyacrylamide(and)C13-14 Isoparaffin(and) Laureth-7, Seppic Corporation, Fairfield, NJ
[3]dimethicone(and)dimethiconol, Dow Corning Corp. Midland, MI
[4]Sorbitan Monostearate and Sucrococoate, ICI Americas Inc., Wilmington, DE
[5]Sucrose ester of fatty acid
[6]DMDM Hydantoin (and) Iodopropynyl Butylcarbamate, Lonza Inc., Fairlawn, NJ

EXAMPLE 3

A series of experiments were conducted to evaluate skin-feel performance through instrumentation. A series of samples were prepared for evaluation in a stick/slip friction test. Base formula for all of the samples was a 20% aqueous glycerin solution thickened with 2% Carbopol 980® into which varying amounts of bis(dihydroxypropyl)dimethylammonium chloride and dimethicone (DC 200/50) were blended.

Measurement of Stick or Tack

A measured amount of each sample (200 microliters) was applied to a one-inch diameter layer of closed cell neoprene mounted on a stainless steel plate. The plate was mounted on the crosshead of an Instron Model 4501 Universal Testing Instrument (Instron Corp., Canton, Mass.). Another one-inch diameter layer of closed cell neoprene was attached to a stainless steel plate, which was mounted to a compression load cell on the Instron's Load Frame. The two layers were compressed at a rate of 10 cm/min to a compression force of 100 grams and then separated at a rate of 10 cm/min. The force of separation is defined as Stick or Tack and is measured in grams. Each sample was run five times.

Measurement of Sliding Friction

An excess amount of each sample was applied to a glass and drawn down to a film of 75 microns thick, 6 inches long and 0.5 inches wide using a drawdown knife. The plate was mounted on the crosshead of an Instron Model 4501 Universal Testing Instrument. An aluminum sled measuring 7.6 cm by 2.5 cm and weighing 19 grams was attached to the Instron's Load Cell. After allowing the film to dry for one minute the sled was pulled across the surface at 10 cm/min. The average amount of work is defined as Sliding Friction and is measured in gram-cm.

Higher numbers for "tack" indicate greater stickiness of the sample. Higher "friction" values relate to increased dry. Thus, lower values for tack and friction indicate better aspects of skinfeel.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein.

What is claimed is:

1. A personal care composition comprising:
   (i) from 0.05% to 30% by weight of a polyhydroxy quaternary ammonium salt of structure (I):

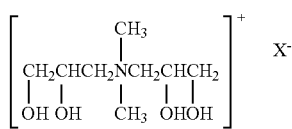

wherein X⁻ is selected from the group consisting of chloride, bromide, hydroxyl, sulphate, phosphate, methosulphate, carboxyl, citrate and tartrate; and
   (ii) from 0.05 to 50% by weight of a silicone.

2. The composition according to claim 1 wherein the polyhydroxy quaternary ammonium salt is a bis(dihydroxypropyl)dimethylammonium chloride.

3. The composition according to claim 1 which is selected from the group consisting of leave-on skin lotions and creams, shampoos, hair conditioners, shower gels, toilette bars, antiperspirants, deodorants, dental products, shave creams, depilatories, lipsticks, foundations, mascara, sunless tanner and sunscreen lotions.

4. The composition according to claim 1 wherein the silicone is a cyclomethicone.

5. The composition according to claim 1 wherein the silicone is dimethicone.

6. The composition according to claim 1 wherein the silicone is a dimethicone/vinyl dimethicone crosspolymer.

7. A method for moisturizing human body parts while still providing an aesthetically pleasing skinfeel comprising topically applying to the human body parts a personal care composition comprising:
   i) from 0.05 to 30% by weight of a polyhydroxy quaternary ammonium having a structure (I):

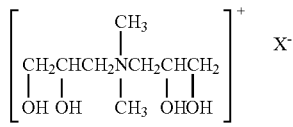

wherein X⁻ is selected from the group consisting of chloride, bromide, hydroxyl, sulphate, phosphate, methosulphate, carboxyl, citrate and tartrate; and
   (ii) from 0.05 to 50% of silicone by weight of the composition.

* * * * *